(12) United States Patent
Blomquist

(10) Patent No.: US 8,219,222 B2
(45) Date of Patent: *Jul. 10, 2012

(54) EXPERT SYSTEM FOR PUMP THERAPY

(75) Inventor: Michael Blomquist, Blaine, MN (US)

(73) Assignee: Smiths Medical ASD, Inc., Rockland, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/774,991

(22) Filed: May 6, 2010

(65) Prior Publication Data

US 2010/0274751 A1    Oct. 28, 2010

Related U.S. Application Data

(63) Continuation of application No. 11/753,420, filed on May 24, 2007, now Pat. No. 7,751,907.

(51) Int. Cl.
- *G05B 11/01* (2006.01)
- *G05B 19/42* (2006.01)
- *A61M 31/00* (2006.01)
- *A61M 37/00* (2006.01)
- *A61M 1/00* (2006.01)

(52) U.S. Cl. ............... 700/83; 700/17; 700/86; 604/66; 604/131; 604/151

(58) Field of Classification Search ............ 700/17, 700/83, 86; 604/66, 131, 151
See application file for complete search history.

(56) References Cited

U.S. PATENT DOCUMENTS

| | | | |
|---|---|---|---|
| 4,393,365 A | 7/1983 | Kondo | |
| 4,475,901 A | 10/1984 | Kraegen et al. | |
| 5,122,362 A | 6/1992 | Phillips et al. | |
| 5,181,910 A | 1/1993 | Scanlon | |
| 5,311,175 A | 5/1994 | Waldman | |
| 5,338,157 A | 8/1994 | Blomquist | |
| 5,364,346 A | 11/1994 | Schrezenmeir | |
| 5,368,562 A | 11/1994 | Blomquist et al. | |
| 5,389,078 A | 2/1995 | Zalesky et al. | |
| 5,485,408 A | 1/1996 | Blomquist | |
| 5,569,186 A | 10/1996 | Lord et al. | |
| 5,658,250 A | 8/1997 | Blomquist et al. | |
| 5,658,252 A | 8/1997 | Johnson | |

(Continued)

FOREIGN PATENT DOCUMENTS

DE    4407005    3/1995

(Continued)

OTHER PUBLICATIONS

"U.S. Appl. No. 11/753,420, Non Final Office Action mailed Jun. 24, 2009", 23 pgs.

(Continued)

*Primary Examiner* — Ronald Hartman, Jr.
(74) *Attorney, Agent, or Firm* — Patterson Thuente Christensen Pedersen, P.A.

(57) ABSTRACT

An apparatus comprising a controller. The controller includes an input/output (I/O) module and a rule module. The I/O module is configured to present a question for a patient when communicatively coupled to a user interface and receive patient information in response to the question via the user interface. The rule module is configured to apply a rule to the patient information and generate a suggested insulin pump setting from application of the rule. Other devices, systems, and methods are disclosed.

6 Claims, 5 Drawing Sheets

U.S. PATENT DOCUMENTS

| | | | |
|---|---|---|---|
| 5,665,065 | A | 9/1997 | Colman et al. |
| 5,669,877 | A | 9/1997 | Blomquist |
| 5,685,844 | A | 11/1997 | Marttila |
| 5,695,473 | A | 12/1997 | Olsen |
| 5,713,856 | A | 2/1998 | Eggers et al. |
| 5,810,771 | A | 9/1998 | Blomquist |
| 5,814,015 | A | 9/1998 | Gargano et al. |
| 5,822,715 | A | 10/1998 | Worthington et al. |
| 5,876,370 | A | 3/1999 | Blomquist |
| 5,879,143 | A | 3/1999 | Cote et al. |
| 5,935,099 | A | 8/1999 | Peterson et al. |
| 5,935,106 | A | 8/1999 | Olsen |
| 6,024,539 | A | 2/2000 | Blomquist |
| 6,077,055 | A | 6/2000 | Vilks |
| 6,241,704 | B1 | 6/2001 | Peterson et al. |
| 6,248,057 | B1 | 6/2001 | Mavity et al. |
| 6,248,067 | B1 | 6/2001 | Causey, III et al. |
| 6,422,057 | B1 | 7/2002 | Anderson |
| 6,475,180 | B2 | 11/2002 | Peterson et al. |
| 6,544,212 | B2 | 4/2003 | Galley et al. |
| 6,551,276 | B1 | 4/2003 | Mann et al. |
| 6,554,798 | B1 | 4/2003 | Mann et al. |
| 6,558,320 | B1 | 5/2003 | Causey, III et al. |
| 6,558,351 | B1 | 5/2003 | Steil et al. |
| 6,562,001 | B2 | 5/2003 | Lebel et al. |
| 6,577,899 | B2 | 6/2003 | Lebel et al. |
| 6,641,533 | B2 | 11/2003 | Causey, III et al. |
| 6,744,350 | B2 | 6/2004 | Blomquist |
| 6,790,198 | B1 | 9/2004 | White et al. |
| 6,809,653 | B1 | 10/2004 | Mann et al. |
| 6,852,104 | B2 | 2/2005 | Blomquist |
| 6,872,200 | B2 | 3/2005 | Mann et al. |
| 6,934,220 | B1 | 8/2005 | Cruitt et al. |
| 6,936,029 | B2 | 8/2005 | Mann et al. |
| 6,979,326 | B2 | 12/2005 | Mann et al. |
| 6,997,920 | B2 | 2/2006 | Mann et al. |
| 7,025,743 | B2 | 4/2006 | Mann et al. |
| 7,033,338 | B2 | 4/2006 | Vilks et al. |
| 7,041,082 | B2 | 5/2006 | Blomquist et al. |
| 7,098,803 | B2 | 8/2006 | Mann et al. |
| 7,109,878 | B2 | 9/2006 | Mann et al. |
| 7,179,226 | B2 | 2/2007 | Crothall et al. |
| 7,267,665 | B2 | 9/2007 | Steil et al. |
| 7,278,983 | B2 | 10/2007 | Ireland et al. |
| 7,291,107 | B2 * | 11/2007 | Hellwig et al. ............... 600/365 |
| 7,307,245 | B2 | 12/2007 | Faries, Jr. et al. |
| 7,324,012 | B2 | 1/2008 | Mann et al. |
| 7,341,577 | B2 | 3/2008 | Gill |
| 7,399,277 | B2 | 7/2008 | Saidara et al. |
| 7,404,796 | B2 * | 7/2008 | Ginsberg ...................... 600/365 |
| 7,515,060 | B2 | 4/2009 | Blomquist |
| 7,559,926 | B1 | 7/2009 | Blischak |
| 7,715,893 | B2 | 5/2010 | Kamath et al. |
| 7,734,323 | B2 | 6/2010 | Blomquist et al. |
| 7,751,907 | B2 | 7/2010 | Blomquist |
| 7,869,851 | B2 * | 1/2011 | Hellwig et al. ............... 600/345 |
| 2001/0031944 | A1 | 10/2001 | Peterson et al. |
| 2001/0037217 | A1 | 11/2001 | Abensour et al. |
| 2002/0002326 | A1 | 1/2002 | Causey, III et al. |
| 2002/0065454 | A1 | 5/2002 | Lebel et al. |
| 2002/0072932 | A1 | 6/2002 | Swamy |
| 2002/0107476 | A1 | 8/2002 | Mann et al. |
| 2002/0183693 | A1 | 12/2002 | Peterson et al. |
| 2002/0193679 | A1 | 12/2002 | Malave et al. |
| 2003/0032867 | A1 | 2/2003 | Crothall et al. |
| 2003/0036683 | A1 | 2/2003 | Kehr et al. |
| 2003/0050621 | A1 | 3/2003 | Lebel et al. |
| 2003/0060765 | A1 * | 3/2003 | Campbell et al. ............. 604/131 |
| 2003/0065308 | A1 | 4/2003 | Lebel et al. |
| 2003/0114836 | A1 | 6/2003 | Estes et al. |
| 2003/0130616 | A1 | 7/2003 | Steil et al. |
| 2003/0160683 | A1 * | 8/2003 | Blomquist ............... 340/309.16 |
| 2003/0163088 | A1 | 8/2003 | Blomquist |
| 2003/0163090 | A1 | 8/2003 | Blomquist et al. |
| 2003/0208113 | A1 | 11/2003 | Mault et al. |
| 2003/0212364 | A1 | 11/2003 | Mann et al. |
| 2004/0015102 | A1 | 1/2004 | Cummings et al. |
| 2004/0068230 | A1 | 4/2004 | Estes et al. |
| 2004/0073095 | A1 | 4/2004 | Causey, III et al. |
| 2004/0115067 | A1 | 6/2004 | Rush et al. |
| 2004/0180810 | A1 | 9/2004 | Pilarski |
| 2004/0254434 | A1 | 12/2004 | Goodnow et al. |
| 2005/0021006 | A1 | 1/2005 | Tonnies |
| 2005/0022274 | A1 | 1/2005 | Campbell et al. |
| 2005/0030164 | A1 | 2/2005 | Blomquist |
| 2005/0050621 | A1 | 3/2005 | Thomas |
| 2005/0065760 | A1 | 3/2005 | Murtfeldt et al. |
| 2005/0095063 | A1 | 5/2005 | Fathallah et al. |
| 2005/0137530 | A1 | 6/2005 | Campbell et al. |
| 2005/0143864 | A1 | 6/2005 | Blomquist |
| 2005/0171513 | A1 | 8/2005 | Mann et al. |
| 2005/0197553 | A1 | 9/2005 | Cooper |
| 2005/0197621 | A1 | 9/2005 | Poulsen et al. |
| 2005/0277872 | A1 | 12/2005 | Colby, Jr. et al. |
| 2006/0001550 | A1 | 1/2006 | Mann et al. |
| 2006/0014670 | A1 | 1/2006 | Green et al. |
| 2006/0047192 | A1 | 3/2006 | Hellwig et al. |
| 2006/0047538 | A1 | 3/2006 | Condurso et al. |
| 2006/0080059 | A1 | 4/2006 | Stupp et al. |
| 2006/0122577 | A1 | 6/2006 | Poulsen et al. |
| 2006/0132292 | A1 | 6/2006 | Blomquist |
| 2006/0137695 | A1 | 6/2006 | Hellwig et al. |
| 2006/0173406 | A1 | 8/2006 | Hayes et al. |
| 2006/0173444 | A1 | 8/2006 | Choy et al. |
| 2006/0202859 | A1 | 9/2006 | Mastrototaro et al. |
| 2006/0224109 | A1 | 10/2006 | Steil et al. |
| 2006/0253097 | A1 | 11/2006 | Braig et al. |
| 2006/0264895 | A1 | 11/2006 | Flanders |
| 2006/0276771 | A1 * | 12/2006 | Galley et al. ................. 604/503 |
| 2007/0016127 | A1 | 1/2007 | Staib et al. |
| 2007/0021733 | A1 | 1/2007 | Hansen et al. |
| 2007/0060796 | A1 | 3/2007 | Kim |
| 2007/0060871 | A1 | 3/2007 | Istoc et al. |
| 2007/0100222 | A1 | 5/2007 | Mastrototaro et al. |
| 2007/0106135 | A1 | 5/2007 | Sloan et al. |
| 2007/0124002 | A1 | 5/2007 | Estes et al. |
| 2007/0156033 | A1 | 7/2007 | Causey, III et al. |
| 2007/0203454 | A1 | 8/2007 | Shermer et al. |
| 2007/0233051 | A1 | 10/2007 | Hohl et al. |
| 2007/0255250 | A1 | 11/2007 | Moberg et al. |
| 2008/0004601 | A1 | 1/2008 | Jennewine et al. |
| 2008/0030369 | A1 | 2/2008 | Mann et al. |
| 2008/0033357 | A1 | 2/2008 | Mann et al. |
| 2008/0051709 | A1 | 2/2008 | Mounce et al. |
| 2008/0051714 | A1 | 2/2008 | Moberg et al. |
| 2008/0071251 | A1 | 3/2008 | Moubayed et al. |
| 2008/0097289 | A1 | 4/2008 | Steil et al. |
| 2008/0106431 | A1 | 5/2008 | Blomquist |
| 2008/0147050 | A1 | 6/2008 | Mann et al. |
| 2008/0172026 | A1 | 7/2008 | Blomquist |
| 2008/0172027 | A1 | 7/2008 | Blomquist |
| 2008/0172028 | A1 | 7/2008 | Blomquist |
| 2008/0172029 | A1 | 7/2008 | Blomquist |
| 2008/0172030 | A1 | 7/2008 | Blomquist |
| 2008/0172031 | A1 | 7/2008 | Blomquist |
| 2008/0177165 | A1 | 7/2008 | Blomquist et al. |
| 2008/0206799 | A1 | 8/2008 | Blomquist |
| 2008/0228056 | A1 | 9/2008 | Blomquist et al. |
| 2008/0269585 | A1 | 10/2008 | Ginsberg |
| 2008/0287922 | A1 | 11/2008 | Panduro |
| 2008/0294294 | A1 | 11/2008 | Blomquist |
| 2008/0300534 | A1 | 12/2008 | Blomquist |
| 2009/0088731 | A1 | 4/2009 | Campbell et al. |
| 2009/0105646 | A1 | 4/2009 | Hendrixson et al. |
| 2009/0131860 | A1 | 5/2009 | Nielsen |
| 2009/0177142 | A1 | 7/2009 | Blomquist et al. |
| 2009/0177147 | A1 | 7/2009 | Blomquist et al. |
| 2009/0177154 | A1 | 7/2009 | Blomquist et al. |
| 2010/0056993 | A1 | 3/2010 | Chase |
| 2010/0057043 | A1 | 3/2010 | Kovatchev et al. |
| 2010/0222765 | A1 | 9/2010 | Blomquist et al. |
| 2010/0312085 | A1 | 12/2010 | Andrews et al. |
| 2011/0033833 | A1 | 2/2011 | Blomquist et al. |
| 2011/0040251 | A1 | 2/2011 | Blomquist |
| 2011/0178717 | A1 | 7/2011 | Goodnow et al. |

FOREIGN PATENT DOCUMENTS

| | | |
|---|---|---|
| DE | 10121317 | 11/2002 |
| DE | 10352456 | 7/2005 |
| EP | 1102194 | 5/2001 |
| EP | 1571582 | 9/2005 |
| WO | WO-0045696 A1 | 8/2000 |
| WO | WO0074753 | 12/2000 |
| WO | WO-0152727 A1 | 7/2001 |
| WO | WO-02062212 A2 | 8/2002 |
| WO | WO-2005046559 A2 | 5/2005 |
| WO | WO2006/061169 | 6/2006 |
| WO | WO2007000425 * | 1/2007 |
| WO | WO-2007056592 A2 | 5/2007 |
| WO | WO2007089537 | 8/2007 |
| WO | WO2007/149533 | 12/2007 |
| WO | WO2008/048582 | 4/2008 |
| WO | WO2008048556 | 4/2008 |
| WO | WO2008048583 | 4/2008 |
| WO | WO2008048584 | 4/2008 |
| WO | WO2008048585 | 4/2008 |
| WO | WO2008048586 | 4/2008 |
| WO | WO2008048587 | 4/2008 |
| WO | WO2008091320 | 7/2008 |
| WO | WO2008/112078 | 9/2008 |
| WO | WO-2008153689 A1 | 12/2008 |
| WO | WO-2008153689 A4 | 12/2008 |
| WO | WO-2008153819 A1 | 12/2008 |
| WO | WO2009088983 | 7/2009 |
| WO | WO2009089028 | 7/2009 |
| WO | WO2009089029 | 7/2009 |

OTHER PUBLICATIONS

"U.S. Appl. No. 11/753,420, Notice of Allowance mailed Feb. 24, 2010", 4.

"U.S. Appl. No. 11/753,420, Response filed Dec. 18, 2009 to Non Final Office Action mailed Jun. 24, 2009", 17 pgs.

"U.S. Appl. No. 11/755,480, Final Office Action mailed Dec. 30, 2009", 14 pgs.

"U.S. Appl. No. 11/755,480, Non-Final Office Action mailed Apr. 30, 2009", 19 pgs.

"U.S. Appl. No. 11/755,480, Respoonse filed Oct. 28, 2009 to Non Final Office Action mailed Apr. 30, 2009", 12 pgs.

"Compare Insulin Pump for Diabetes", printed from www.diabetesnet.com, (Jun. 18, 2009), 4 pages.

"Deltec Cozmo. Personalized Insulin Pump. Starting Guide", *Smith Medical MD Inc.*, [Online]. Retrieved From Internet: <URL:Http://web.archive.org/web/20041207133223/http://www.cozmore.com/Library/upload/starting_guide_032004.pdf>, (Dec. 7, 2004), pp. 1-83.

"International Application Serial No. PCT/US2008/006449, International Search Report mailed Oct. 10, 2008", 8 pgs.

"International Application Serial No. PCT/US2008/006449, Written Opinion mailed Oct. 10, 2008", 7 pgs.

"International Application Serial No. PCT/US2008/006801, International Search Report mailed on Oct. 30, 2008", 8 pgs.

"International Application Serial No. PCT/US2008/006801, Written Opinion mailed on Oct, 30, 2008", 8 pgs.

"Wikipedia's definition for "basal rate"", printed from wikipedia.com on Jun. 12, 2009., (Jun. 12, 2009), 1 page.

Blomquist, Mike, et al., "Basal Rate Testing Using Frequent Blood Glucose Input", U.S. Appl. No. 11/685,617, filed Mar. 13, 2007, 44 pgs.

Blomquist, Mike, "Carbohydrate Ratio Testing Using Frequent Blood Glucose Input", U.S. Appl. No. 11/679,712, filed Feb. 27, 2007, 51 pgs.

Blomquist, Mike, et al., "Correction Factor Testing Using Frequent Blood Glucose Input", U.S. Appl. No. 11/626,653, filed Jan. 24, 2007, 41 pgs.

Blomquist, Mike, "Expert System for Insulin Pump Therapy", U.S. Appl. No. 11/753,420, filed May 24, 2007, 34 pgs.

Blomquist, Mike, "Insulin Pump Based Expert System", U.S. Appl. No. 11/755,480, filed May 30, 2007, 41 pgs.

Walsh, John, et al., "Title Page, Citation page and Table of Contents", *Pumping Insulin: Everything You Need for Success on a Smart Insulin Pump*, Torrey Pines Press, San Diego. ISBN 1-884804-86-1, (2006), Title page, ii, ix.

Plougmann et al, "DiasNet—a diabetes advisory system for communication and education via the internet", International Journal of Medical Informatics, vol. 26. pp. 319-330 (2001).

Wilinska et al., "Insulin Kinetics in Type-1 Diabetes: Continuous and Bolus Delivery of Reapid Acting Insulin>" IEEE Transactions on Bopmedical Engineering vol. 52. No. 1, pp. 3-12. Jan. 2005.

Bott et al, "Impact of Smoking on the Metabolic Action of Subcutaneous Regular Insulin in Type 2 Diabetic Patients" Horm. Metab. Res., vol. 37, pp. 445-449 (2005).

Puckett et a l., Am. J. Physiol. vol. 269, p. E1115-E1124, 1995.

Wach et al., Med & Biol. Eng & comput., vol. 33, p. 18-23, 1995.

Lehman et al., Artifical Intelligence in Medicine, vol. 6, p. 137-160, 1994.

"The Use of Insulin Pumps With Meal Bolus Alarms in Children With Type 1 Diabetes to Improve Glycemic Control", Diabetes Carem vol. 29, No. 5. May 2006. 1012-1015.

European Office Action from European Application No. 08779626.4 mailed May 25, 2010.

European Office Action from Europrean Application No. 08767734.6 dated Apr. 7, 2010.

International Search Report for International Application No. PCT/US2007/022050 mailed Mar. 7, 2008.

International Search Report for International Application No. PCT/US09/00107 dated May 4, 2009.

International Search Report for International Application No. PCT/US2007/024424 mailed Mar. 6, 2009.

International Search Report for International Application No. PCT/US2008/002536 dated Sep. 4, 2008.

International Search Report for International Application No. PCT/US2009/000034 dated May 27, 2009.

International Search Report for International Application No. PCT/US2009/000106 dated May 13, 2009.

International Search Report from International Application No. PCT/US2007/024423 dated May 19, 2008.

Stapel, Elizabeth, "Converting Between Decimals, Fractions, and Percents", Purplemath. 2006. http://www.purplemath.com/modules/percents2.htm.

Walsh et al., "Diabetes Technology—Concept 1: Super Bolus" (online) http://www.diabetesnet.com/diabetes_technology/super_bolus.php>. Sep. 17, 2007. 3 pages.

Walsh et al., "Select & Test Your Basal Rates", Pumping Insulin, Fourth Edition, Chapter 11 (2006). 30 pages.

Walsh et al., "Select & Test Your Correction Factor", Pumping Insulin, Fourth Edition, Chapter 13. (2006).

Written Opinion for International Application No. PCT/US09/00107 dated May 4, 2009.

Written Opinion for International Application No. PCT/US2007/022050 mailed Mar. 7, 2008.

Written Opinion for International Application No. PCT/US2007/024424 mailed Mar. 6, 2009.

Written Opinion for International Application No. PCT/US2008/002536 dated Sep. 4, 2008.

Walsh et al., "Select and Test Your Carb Factor", Pumping Insulin, Fourth Edition, Chapter 12. (2006). 32 pages.

Written Opinion for International Application No. PCT/US2009/000034 dated May 27, 2009.

Written Opinion for International Application No. PCT/US2009/000106 dated May 13, 2009.

Written Opinion from International Application No. PCT/US2007/024423 dated May 19, 2008.

International Search Report for International Application No. PCT/US2007/022046 dated Mar. 7, 2008.

Written Opinion for International Application No. PCT/US2007/022046 dated Mar. 7, 2008.

Trajanoski et al., Pharmacokinetic Model for the Absorption of Subcutaneoutsly Injected Soluble Insulin and Monomeric Insulin Analogues. Biomedizinische Technik,. vol. 38 No. 9. Sep. 1, 1993.

Hildebrandt, Subcutaneous Absorption of Insulin in Insulin-Dependent Diavetic patients. Influence of Species Physico-Chemcial properties of Insulin and Physiological factors. Danish Medical Bulletin. Aug. 1991.

Written Opinion for International Application No. PCT/US2007/022004 dated Oct. 9, 2008.

International Search Report for International Application No. PCT/US2007/022004 dated Oct. 9, 2008.
Written Opinion for International Application No. PCT/US2007/022047 dated Mar. 7, 2008.
International Search Report for International Application No. PCT/US2007/022047 dated Mar. 7, 2008.
Written Opinion for International Application No. PCT/US2007/022048 dated Mar. 7, 2008.
International Search Report for International Application No. PCT/US2007/022048 dated Mar. 7, 2008.
Written Opinion for International Application No. PCT/US2007/022049 dated Mar. 7, 2008.
International Search Report for International Application No. PCT/US2007/022049 dated Mar. 7, 2008.
International Search Report for International Application No. PCT/US2007/022051 dated Mar. 7, 2008.
Written Opinion for International Application No. PCT/US2007/022051 mailed Mar. 7, 2008.
International Search Report for International Application No. PCT/US2007/022052 dated May 11, 2007.
Written Opinion for International Application No. PCT/US2007/022052 mailed May 11, 2007.
European Office Action from European Application No. 07852760.3 dated Aug. 11, 2010.
Application and File Wrapper for U.S. Appl. No. 11/582,841, filed Oct. 17, 2006, inventor Blomquist.
Application and File Wrapper for U.S. Appl. No. 11/626,653, filed Jan. 24, 2007, inventors Blomquist et al.
Application and File Wrapper for U.S. Appl. No. 11/753,420, filed May 24, 2007, inventor Blomquist.
Application and File Wrapper for U.S. Appl. No. 12/720,306, filed Mar. 9, 2010 inventors Blomquist et al.
Application and File Wrapper for U.S. Appl. No. 11/018,706, filed Dec. 20, 2004, inventor Blomquist.
Application and File Wrapper for U.S. Appl. No. 11/582,519, filed Oct. 17, 2006, inventor Blomquist.
Application and File Wrapper for U.S. Appl. No. 11/582,823, filed Oct. 17, 2006, inventor Blomquist.
Application and File Wrapper for U.S. Appl. No. 11/970,232, filed Jan. 7, 2008, inventor Blomquist.
Application and File Wrapper for U.S. Appl. No. 11/679,712, filed Feb. 27, 2007 inventor Blomquist.
Application and File Wrapper for U.S. Appl. No. 11/685,617, filed Mar. 13, 2007 inventor Blomquist et al.
Application and File Wrapper for U.S. Appl. No. 11/755,480, filed May 30, 2007, inventor Blomquist.
Application and File Wrapper for U.S. Appl. No. 11/971,351, filed Jan. 9, 2008 inventor Blomquist.
Application and File Wrapper for U.S. Appl. No. 11/970,691, filed Jan. 8, 2008, inventor Blomquist.
Application and File Wrapper for U.S. Appl. No. 12/908,218, filed Oct. 20, 2010 inventor Blomquist.
Application and File Wrapper for U.S. Appl. No. 12/914,295, filed Oct. 28, 2010 inventor Blomquist.
Application and File Wrapper for U.S. Appl. No. 11/582,831, filed Oct. 17, 2006, inventor Blomquist.
Application and File Wrapper for U.S. Appl. No. 11/582,845, filed Oct. 17, 2006, inventor Blomquist.
Application and File Wrapper for U.S. Appl. No. 11/582,877, filed Oct. 17, 2006, inventor Blomquist.
Application and File Wrapper for U.S. Appl. No. 11/582,879, filed Oct. 17, 2006, inventor Blomquist.

* cited by examiner

US 8,219,222 B2

EXPERT SYSTEM FOR PUMP THERAPY

TECHNICAL FIELD

The field generally relates to patient insulin management devices and, in particular, but not by way of limitation, to systems, devices and methods for managing insulin therapy.

BACKGROUND

People who suffer from diabetes require insulin to keep their blood glucose level as close as possible to normal levels. It is essential for people with diabetes to manage their blood glucose level to within a normal range. Complications from diabetes can include heart disease (cardiovascular disease), blindness (retinopathy), nerve damage (neuropathy), and kidney damage (nephropathy). Insulin is a hormone that reduces the level of blood glucose in the body. Normally, insulin is produced by beta cells in the pancreas. In non-diabetic people, the beta cells release insulin to satisfy two types of insulin needs. The first type is a low-level of background insulin that is released throughout the day. The second type is a quick release of a higher-level of insulin in response to eating. Insulin therapy replaces or supplements insulin produced by the pancreas.

Conventional insulin therapy typically involves one or two injections a day. The low number of injections has the disadvantage of allowing larger variations in a person's insulin levels. Some people with diabetes manage their blood glucose level with multiple daily injections (MDI). MDI may involve more than three injections a day and four or more blood glucose tests a day. MDI offers better control than conventional therapy. However, insulin injections are inconvenient and require a diabetic person to track the insulin doses, the amount of carbohydrates eaten, and their blood glucose levels among other information critical to control.

It is important for a diabetic person to be treated with the proper amount of insulin. As discussed previously, high blood sugar can lead to serious complications. Conversely, a person with low blood sugar can develop hypoglycemia. Ideally, insulin therapy mimics the way the body works. An insulin pump is one way to mimic the body's insulin production. An insulin pump can provide a background or basal infusion of insulin throughout the day and provide a quick release or bolus of insulin when carbohydrates are eaten. If a person develops high blood sugar, a correction bolus can be delivered by the pump to correct it. While insulin pumps improve convenience and flexibility for a diabetic person, they can be sophisticated devices. Some insulin pumps can be difficult to program. Proper use of an insulin pump requires a user to go through a learning curve to properly treat their diabetes using the insulin pump.

SUMMARY

This document discusses, among other things, devices and methods for managing insulin therapy. A device example includes a controller. The controller includes an input/output (I/O) module and a rule module. The I/O module is configured to present a question for a patient when communicatively coupled to a user interface and receive patient information in response to the question via the user interface. The rule module is configured to apply a rule to the patient information and generate a suggested insulin pump setting from application of the rule.

A method example includes presenting a question for a diabetic patient using a device, receiving patient information into the device in response to the question, applying a rule to the patient information, and generating a suggested insulin pump setting from application of the rule.

This summary is intended to provide an overview of the subject matter of the present patent application. It is not intended to provide an exclusive or exhaustive explanation of the invention. The detailed description is included to provide further information about the subject matter of the present patent application.

DETAILED DESCRIPTION

The following detailed description includes references to the accompanying drawings, which form a part of the detailed description. The drawings show, by way of illustration, specific embodiments in which the invention may be practiced. These embodiments, which are also referred to herein as "examples," are described in enough detail to enable those skilled in the art to practice the invention. The embodiments may be combined, other embodiments may be utilized, or structural, logical and electrical changes may be made without departing from the scope of the present invention. The following detailed description is, therefore, not to be taken in a limiting sense, and the scope of the present invention is defined by the appended claims and their equivalents.

In this document, the terms "a" or "an" are used, as is common in patent documents, to include one or more than one. In this document, the term "or" is used to refer to a nonexclusive or, such that "A or B" includes "A but not B," "B but not A," and "A and B," unless otherwise indicated. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

Figure 1A:
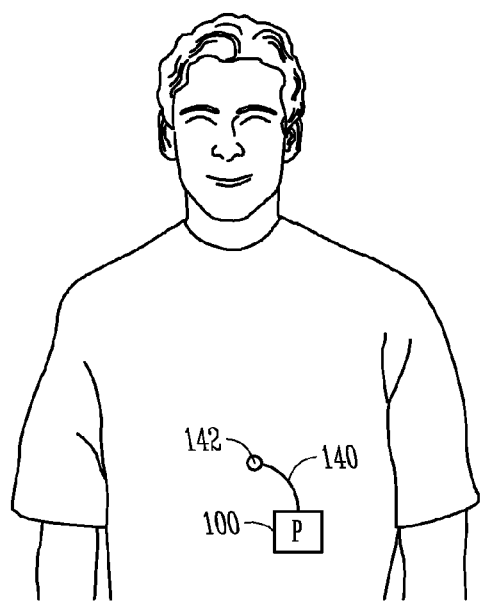
FIGS. 1A and 1B illustrate portions of a device that includes an insulin pump.
Figure 1B:
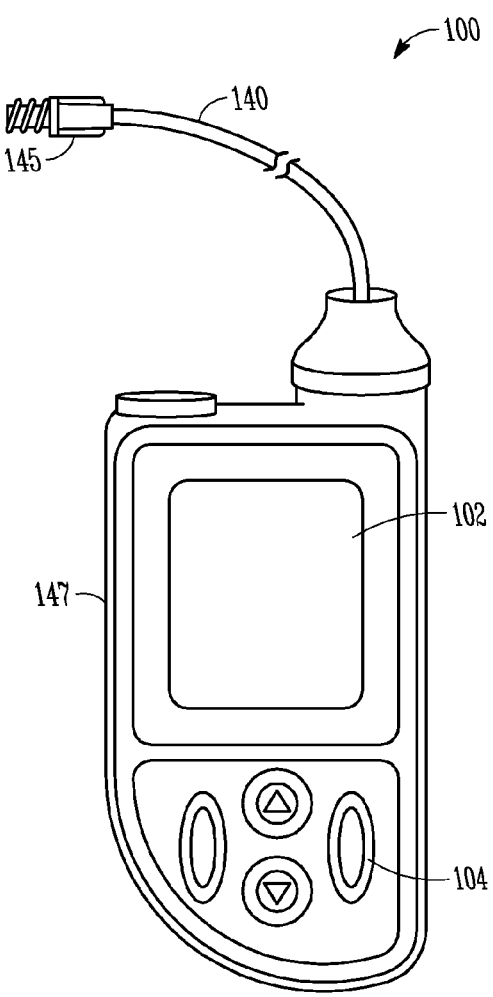

FIGS. 1A and 1B illustrate portions of a device 100 that includes an insulin pump. The device 100 includes a cassette or cartridge of insulin. The cartridge is connectable to infusion tubing 140 connectable to a patient such as by a Luer lock 145 or infusion set 142. The device 100 includes a display 102 and a user interface that may include the display 102 and include one or more keys 104. Because proper use of an insulin pump requires a user to go through a learning curve to properly treat their diabetes using the pump, it is desirable for a pump to provide assistance to the user, whether the user is a diabetic patient, a caregiver, or a clinician. An expert system provides assistance or coaching to the user to effectively treat their diabetes using the insulin pump device.

Figure 2:
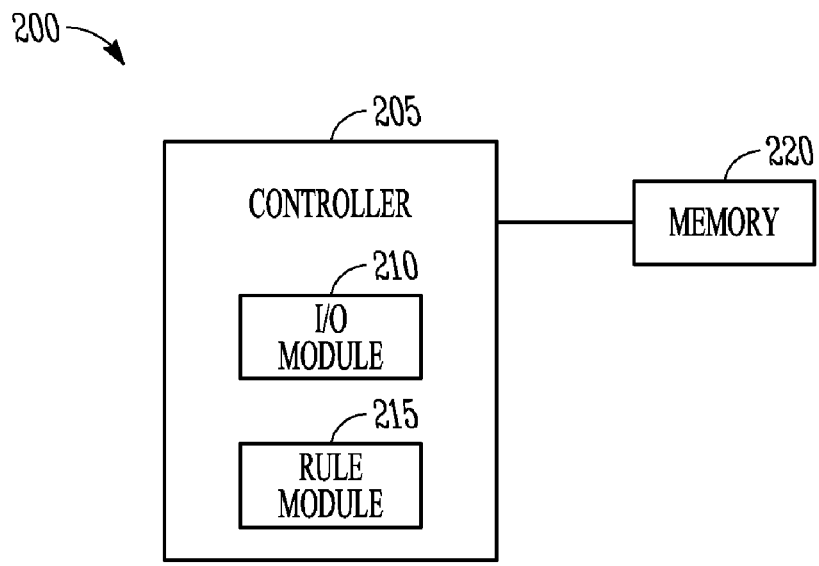
FIG. 2 is a block diagram of an example of portions of a device to provide assistance in maintaining and adjusting a patient's insulin pump therapy.

FIG. 2 is a block diagram of an example of portions of a device 200 to provide assistance in maintaining and adjusting a patient's insulin pump therapy. The device 200 includes a controller 205. The controller 205 can be implemented using hardware circuits, firmware, software or any combination of hardware, firmware and software. Examples, include a microcontroller, a logical state machine, and a processor such as a microprocessor, application specific integrated circuit (ASIC), or other type of processor. The controller 205 is configured to perform or execute a function or functions. Such functions correspond to modules, which are software, hardware, firmware or any combination thereof. Multiple functions may be performed in one or more modules. In some examples, software or firmware is provided on a computer readable medium. The computer readable includes instructions therein, which when processed (such as by the controller 205 for example) results in a device performing the functions described herein. Examples of a computer readable medium include a compact disc (CD), memory stick, or remote storage accessible via a communication network such as the internet or a cell phone network.

The controller 205 includes an input-output (I/O) module 210. The I/O module 210 presents a question for a patient when the I/O module 210 is communicatively coupled to a user interface. The user interface may include one or more pushbuttons or a keypad. The user interface may include a display to visually present instructions and/or the question to the user. The user of the device 200 may be a clinician or a diabetic patient. The display may include a touch-screen. The user interface may include a speaker to present instructions and questions audibly. A speaker may be desirable when the user has difficulty in reading a display.

The I/O module 210 receives patient information in response to the question via the user interface. In some examples, the question and response is included in a series of questions and responses that are part of a patient interview by the device 200. A patient interview may cover a broad range of information. In some examples, the patient information may include patient health information such as a patient health status or whether the patient has any other health-related conditions. The health information also may include whether information concerning any drugs or medications the patient may be taking. Some drugs may cause a person to need more insulin, or the patient may be taking a drug to slow down the absorption of food.

The patient information may include patient lifestyle information. The lifestyle information may include whether a patient tends to eat high glycemic index foods, drinks alcohol, smokes, eats a bedtime snack, a health status of the patient, whether the patient is typically under stress, whether the patient tends to be active, and the amount time the patient spends exercising, for example. The patient information may include patient demographic information. The demographic information may include a patient's weight, age, and gender for example.

In some examples, the patient information may be stored in a memory 220 communicatively coupled to the controller 205. The information may be stored in response to the questions or may be pre-stored in the device 200. The controller 205 includes a rule module 215. The rule module 215 applies a rule to the patient information and generates a suggested insulin pump setting from application of the rule. In some embodiments, the rule includes a decision tree. A decision tree may be implemented with a series of IF-Then logic statements. The controller 205 traverses the decision tree using the patient information. In some embodiments, the rule module 215 may include a look-up table stored in the memory 220. The look-up table may have entries that include one or more insulin pump settings. The table may include multiple dimensions to take into account multiple factors, responses, or other information.

An example of an insulin pump setting is a basal rate. Basal rate refers to a type of twenty-four hour background infusion of insulin by an insulin pump that mimics the continuous background release of insulin from a normal pancreas. It is the rate of insulin delivery the patient normally needs independent of the consumption of meals. The basal rate is typically specified in insulin units per hour (u/hr). The patient information may include a total daily dose (TDD) of insulin, or the rule module may determine a TDD from patient information including the type of diabetes of the patient and the patient's weight, age, and level of fitness. The rule included in the rule module 215 may determine that the amount of daily basal insulin according to a percentage of TDD, such as 40%, 50%, or 60% for example. The percentage applied by the rule may be customized according to the preferences of a clinician. The TDD is then divided by 24 to obtain an average hourly basal rate. For example, if a patient's TDD is determined to be 40 units of insulin, and 50% of the TDD is used for basal delivery, the rule module 215 determines that the average basal rate is 20 units/24 hours or 0.83 u/hr.

Many insulin pump users may use three or more different basal rates during the course of a day. Basal rates can be adjusted to change delivery every few minutes (e.g., 20-30 minutes) by increments as small as 0.05 u/hr to better track changes in demand, such as from an increase typically needed before dawn or a decrease needed during long active periods. The device 200 provides assistance in determining one or more basal rates for the patient. For example, the rule may be a look-up table that includes one or more basal rates indexed by an activity level of the patient. The rule determines a lower basal rate during an increased activity level of the patient. In another example, the rule may increase a basal rate during times when the patient takes a drug that causes the patient to need more insulin. In yet another example, the rule may decrease a basal rate or a segment of a basal rate pattern if the patient is taking a drug to delay the digestion of food.

Another example of an insulin pump setting is a correction factor. A correction factor refers to the amount in drop in blood sugar, or blood glucose, for one unit of insulin. It is measured in milligrams per deciliter (mg/dl) per unit in the U.S. and in millimoles (mmol) per unit in other countries. An insulin pump may use the correction factor to automatically determine a bolus amount required for a high reading or a reduction in a meal bolus for a below-target reading. The insulin pump may also use the correction factor to calculate the amount of carbohydrates a patient should eat to bring low blood sugar up to a target blood sugar level. An appropriate correction factor brings a high blood glucose reading down using an automatically determined correction bolus without a risk of going low.

The rule module 215 may include a rule such as the "1800 rule" in setting the correction factor. For example, if a person's TDD is 40 units of insulin, the correction factor would be 1800/40, or 45 mg/dl per unit. (The 1800 rule corresponds to a "100 rule" if mmol are used.) The rule module 215 may also take into account factors such as a person's age, weight, and activity level when setting the correction factor. Other rules include the 1700 rule (94 rule if mmol) and the 1500 rule (83 rule if mmol). For example, under the 1700 rule the correction factor would be 1700/40 or 42.5 mg/dl. A clinician may prefer one rule over another based on experience including rules that are not based on TDD. The rule to determine the correction factor may be customized according to the preferences of the clinician.

Another example of an insulin pump setting is a carbohydrate ratio. A carbohydrate ratio refers to the amount of carbohydrates covered by a unit of insulin. It is sometimes referred to as a carbohydrate factor, or carb factor, and is typically specified as grams of carbohydrates per unit of insulin. An insulin pump device may use the carbohydrate ratio to automatically determine a carbohydrate insulin bolus amount required to match a number of carbohydrates ingested by the patient, or at least to keep post-meal blood glucose within a range that is healthy for a patient. For example, the patient may plan to eat seventy grams of carbohydrates. If the carbohydrate ratio is ten grams of carbohydrates per unit of insulin, the insulin pump may determine that seven units of insulin are required to cover the carbohydrates.

The rule module 215 may include a formula such as the "500 rule" in setting the carbohydrate ratio. For example, if a person's TDD is 40 units of insulin, the carbohydrate ratio would be 500/40 or about 13 grams per unit of insulin. The rule module 215 may also take into account factors such as a person's age, weight, and activity level when setting the carbohydrate ratio. Other formulas include the 550 rule and the 600 rule. For example, under the 600 rule the carbohydrate ratio would be 600/40 or 15 grams per unit of insulin. As discussed above, the larger the carbohydrate ratio, the smaller a carbohydrate bolus becomes. Because a clinician may prefer one rule over another based on experience; including rules that are not based on TDD, the rule to determine the correction factor may be customized according to the preferences of the clinician.

According to some examples, the memory 220 may store parameters associated with an insulin pump initial setup. The rule module 215 applies a rule to match the insulin pump parameters to at least one of patient health information, patient lifestyle information, and patient demographic information to generate a suggested insulin pump initial setup. The rule module 215 may apply the rule to the patient information to determine at least one of an initial correction factor, an initial carbohydrate ratio, and one or more initial basal rate patterns or profiles. For example, as part of the device interview a patient may enter those periods when the patient regularly exercises into the device 200. The rule may generate different basal rates before, during, or after the exercise periods. In another example, the patient enter the fact that she is pregnant or trying to get pregnant into the device 200. The rule may suggest more aggressive correction bolus targets. In a further example, based on the demographic data the rule may determine different insulin pump initial setups for children, teens, adult females, adult males, and seniors. The demographic information would initially setup parameters including basal rates, carbohydrate bolus limits, insulin pump feature lockouts and enables.

Figure 3:
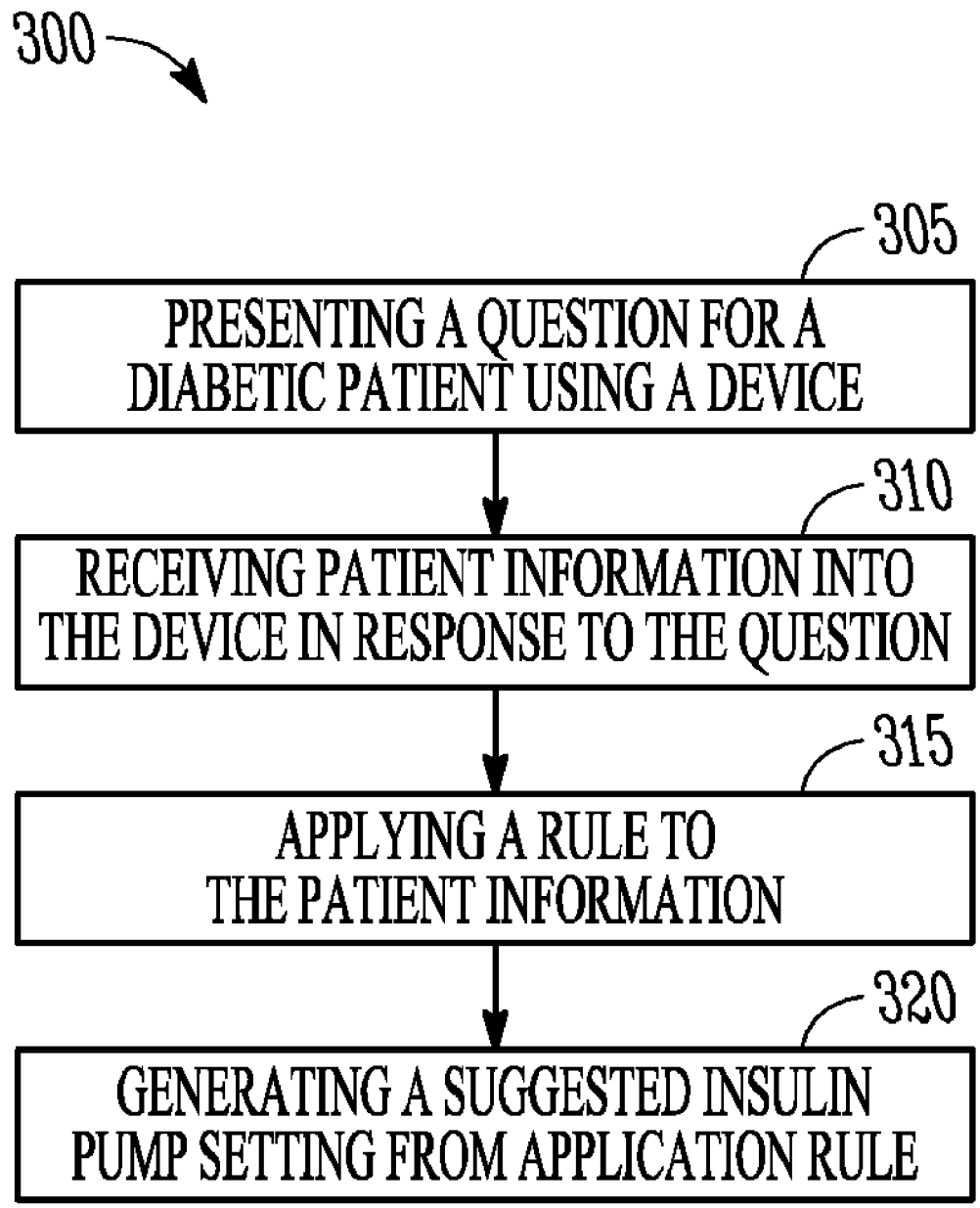
FIG. 3 shows a flow diagram of a method to provide assistance in maintaining and adjusting a patient's insulin pump therapy.

FIG. 3 shows a flow diagram of a method to provide assistance in maintaining and adjusting a patient's insulin pump therapy. At block 305, a question is presented for a diabetic patient using a device. At block 310, patient information is received into the device in response to the question. At block 315, a rule is applied to the patient information. At block 320, a suggested insulin pump setting is generated from application of the rule.

Figure 4:
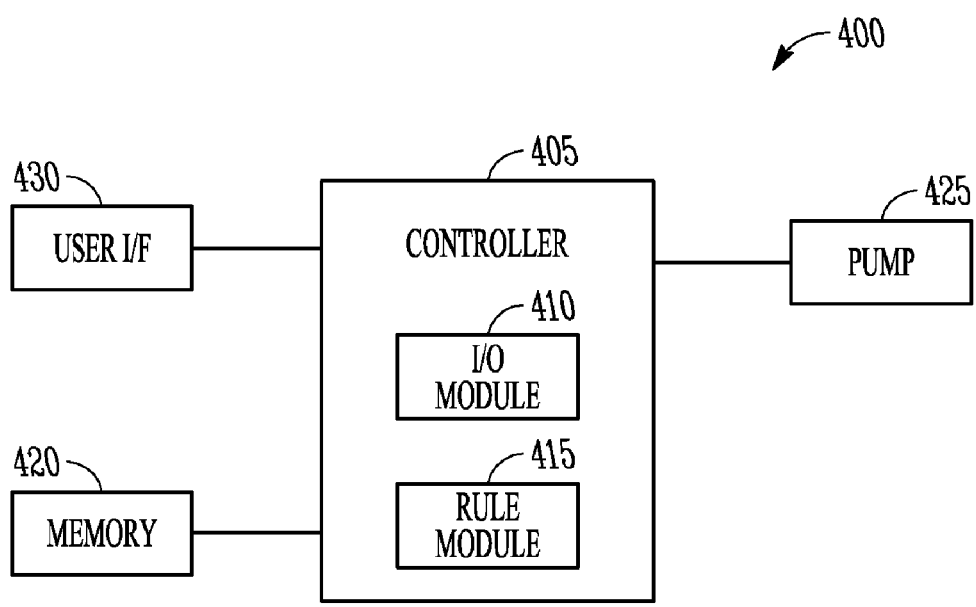
FIG. 4 is a block diagram of another example of portions of a device to provide assistance in maintaining and adjusting a patient's insulin pump therapy.

FIG. 4 is a block diagram of another example of portions of a device 400 to provide assistance in maintaining and adjusting a patient's insulin pump therapy. The device 400 includes an insulin pump 425 or pump mechanism to deliver insulin to a patient, such as a positive displacement pump for example. The device 400 also includes a controller 405 communicatively coupled to a memory 420. The controller 405 includes an I/O module 410 and a rule module 415. The memory 420 may store parameters associated with insulin pump therapy. The rule module 415 applies a rule to generate a suggested insulin pump initial setup.

The device 400 includes a user interface 430 communicatively coupled to the I/O module 410. In some examples, the user interface 430 includes a display and the I/O module 410 presents one or more suggested insulin pump settings to the user via the user interface 430. The I/O module additionally presents a request to the user for confirmation of the insulin pump setting. After a request is received, the setting or settings are adopted or activated by the device 400, such as by moving the settings from the memory 420 to operating registers for example.

Figure 5:
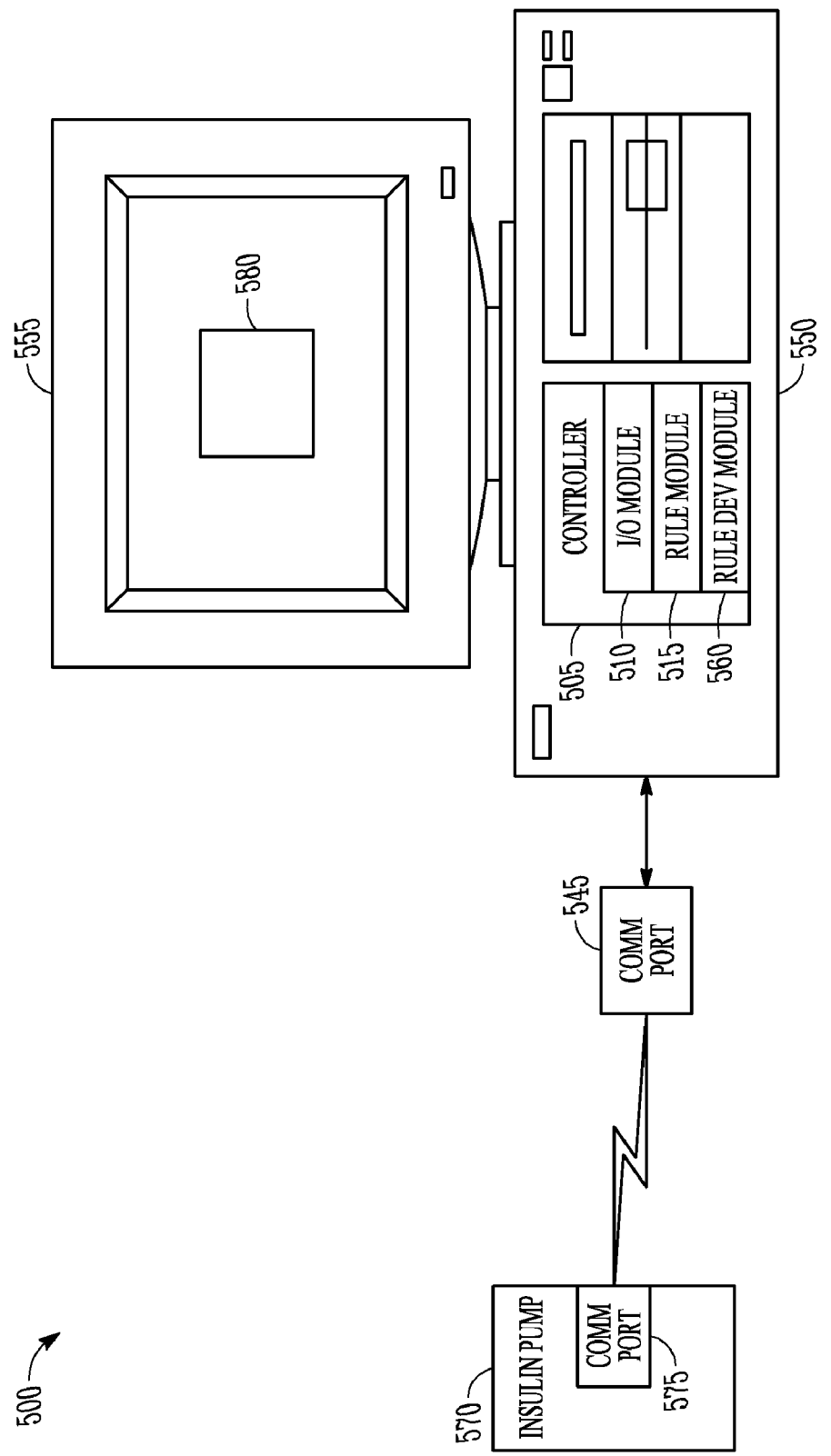
FIG. 5 is a diagram of yet another example of portions of a device to provide assistance in maintaining and adjusting a patient's insulin pump therapy.

FIG. 5 is a diagram of an example of a device 500 to provide assistance in maintaining and adjusting a patient's insulin pump therapy. The device 500 includes a computing device 550. Examples of a computing device 550 include among other things a personal computer (PC), laptop computer, and personal data assistant (PDA). The computing device 550 includes a controller 505. The controller 505 includes an I/O module 510 and a rule module 515. The computing device 550 also includes a user interface 555 that includes a display and may include at least one of a keyboard or keypad and a computer mouse. The computing device 550 further includes a communication port 545 communicatively coupled to the I/O module 510. The device 500 communicates information with an insulin pump 570 via the communication port 545. In some examples, the communication port 545 is a wireless port and the device 500 communicates with the insulin pump 570 using wireless signals, such as a radio frequency (RF) port or infrared (IR) port for example. In some examples, the communication port 545 is a wired port (e.g., a serial port) and the device 500 communicates with the insulin pump using a removable communication cable.

The rule module 515 applies a rule to generate at least one insulin pump setting. The I/O module 510 presents the setting to a user as a suggested insulin pump setting via the user interface 555. The I/O module 510 also presents a request for confirmation of the insulin pump setting. When the I/O module 510 receives a confirmation, such as through the user interface 555 for example, the I/O module 510 communicates the insulin pump setting to the insulin pump 570 via the communication port 545.

As set forth previously, a rule may be customized. In some examples, the controller 505 includes a rule development module 560 to develop a rule via edits received via the I/O module 510. The rule development module 560 is a rule editor that edits existing rules in addition to generating new rules. In some examples, the rule development module 560 displays a representation 580 of the rule when the I/O module 510 is communicatively coupled to the user interface 555. The rule development module 560 converts a manipulation of the displayed representation 580 via the user interface into the edit to the rule.

The rule development module 560 provides doctors or clinical experts the ability to develop and generate a new rule (or rule set) or to modify rules via the user interface 555. The computing device 550 includes software that provides a flexible framework to create or modify rules such as by updating a graphical decision tree or a look-up table for example. The software may be included in a computer readable medium, such as a compact disc (CD) for example, or the software may be downloaded to the computing device 550 from remote storage, such as from a server for example. The computing device 550 uses the communication port 545 to communicate the rule or rule set to the insulin pump 570.

Once a rule is developed, the doctor or clinical expert could publish or otherwise share a rule or set of rules. In some embodiments, rule sets can be stored in remote storage, such as a server for example. The computing device 550 may be connected to a communication network, such as the internet or a cell phone network for example. A doctor or clinical expert may download a rule or rule set from the remote storage and either download the rule set directly from the computing device 550 into the insulin pump device 570 or modify the rule or rule set before downloading the modified rule or rule set to the insulin pump device 570.

Returning to FIG. 4, the controller 405 may include a rule development module. The user interface 430 receives edits to a rule or rule set. The edits are entered into the device 400 manually by the user via the user interface 430. For example, the user may step through the rule with the aid of a display included in the user interface 430. The user may then alter the rule with a keypad included in the user interface 430. For example, the user may enter a new look up table entry using the key pad, or add another branch to a decision tree or edit a branch of the decision tree. In certain examples, an entire new rule or rule set is entered manually into the device 400 via the user interface 430.

In some examples, the device 400 of FIG. 4 or the insulin pump device 570 of FIG. 5 stores data to track effectiveness of a new rule or modified rule. For example, the insulin pump device 570 may track the number of times the blood glucose level of the patient returned to a target blood glucose level or to within a target range of levels after application of the rule. The effectiveness may be displayed as a percentage or as X successes out of Y applications on either a display of the insulin pump device 570 or uploaded and displayed on a separate device, such as the computing device 550 in FIG. 5 for example.

Returning to the device of FIG. 2, in some examples, the rule module 215 assigns weights to corresponding table entries in a rule. For example, a certain type of exercise (e.g. higher intensity) may be weighted higher when determining whether to suggest a different basal rate for the patient during the exercise (versus suggesting a food to eat before exercise of lower intensity). In some examples, the rule module 215 uses one or more fuzzy logic rules to determine the question for display and any recommended action. The fuzzy logic rules may be used to blend any weighted questions, responses, or actions. In some examples, the rule module 215 uses a rule involving application of artificial intelligence methods to determine the questions and the actions to be presented. In some examples, the weighting used by the rule is customizable.

In some examples, the memory 220 stores a database of food options in association with a known amount of nutrient content. The rule module 215 uses the patient health, lifestyle, and demographic information set forth above and generates a suggested database of food options. For example, if the patient lifestyle information indicates that the patient tends to eat high glycemic index foods, or the patient health information indicates that the patient is pregnant, the suggested database may include mostly low glycemic foods. If the controller 205 is included in a computing device 550 of FIG. 5 or other type of device, that device communicates the suggested database to the insulin pump device 570 where it is stored. If the controller 205 is included in an insulin pump device as in FIG. 4, the controller 405 only displays the suggested portion of the database to a user.

Without an expert system, a pump user may go through several iterations of trial and error in finding appropriate insulin pump settings. In some examples, the device 200 uses blood glucose information as feedback to better tune insulin pump settings. The rule module 215 applies the rule to blood glucose information, such as blood glucose data taken using a blood glucose monitor (GM), to determine one or more insulin pump settings.

The I/O module 210 may present an action for the user to take. In some examples, the action presented may be a prompt for the user to enter blood glucose data into the device, download blood glucose data into the device, or to begin a blood glucose measurement. For example, the action presented may be a prompt to measure blood glucose level from a finger stick and to enter the data into the I/O module 210 through a user interface. In some examples, the device 200 includes a communication port communicatively coupled to the controller 205. The I/O module 210 receives the blood glucose data via the communication port from a second separate device that includes a glucose monitor. In some examples, the communication port includes a wireless communication port. A separate device may obtain the blood glucose data during a test executed using an insulin pump. In some examples, the device 200 includes an insulin pump communicatively coupled to the controller 205.

Figure 6:
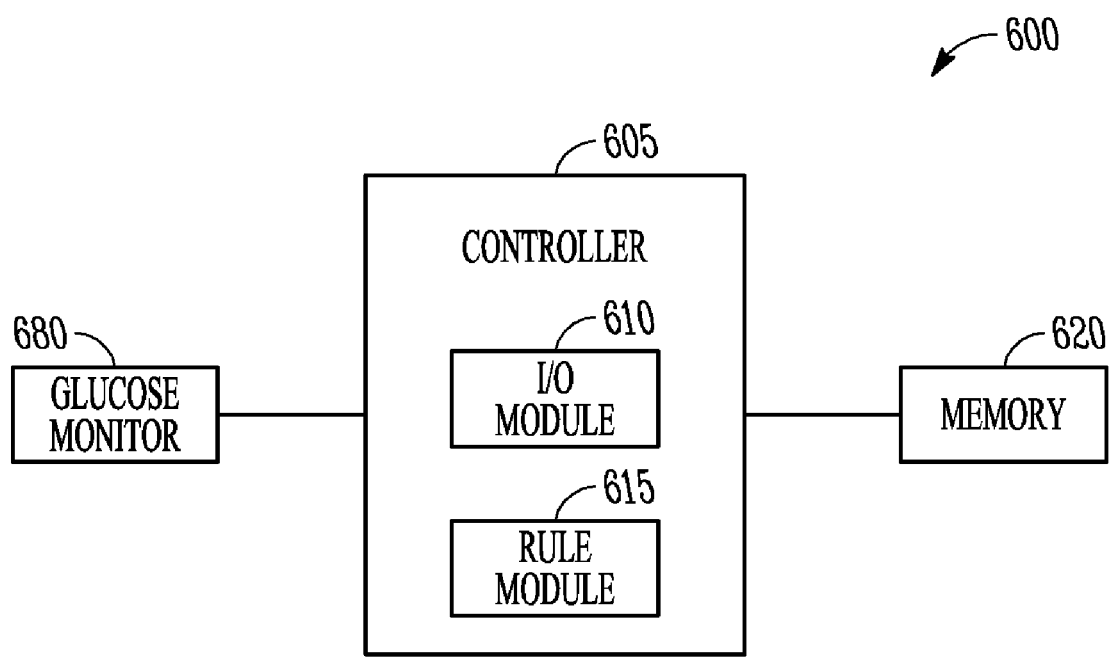
FIG. 6 is a block diagram of a further example of portions of a device to provide assistance in maintaining and adjusting a patient's insulin pump therapy.

In some examples, the device 200 includes a GM. FIG. 6 is a diagram of another example of a device 600 to provide assistance in maintaining and adjusting a patient's insulin pump therapy. The device 600 includes a controller 605 communicatively coupled to a memory 620. The controller 605 includes an I/O module 610 and a rule module 615. The device also includes a GM 680 communicatively coupled to the controller 605. In some examples, the device 600 also includes an insulin pump communicatively coupled to the controller 605.

If the GM 680 is a continuous GM, no action is needed from the user to obtain blood glucose data. A continuous GM includes a blood glucose sensor to produce a blood glucose signal representative of a blood glucose level of the patient. The blood glucose sensor may sense blood glucose concentration from blood or interstitial fluid. The blood glucose sensor circuit may include a sensor interface circuit to sample the blood glucose signal and may provide additional signal processing such as filtering or amplification for example. The blood glucose sensor circuit may provide sampled blood glucose data to the I/O module 610. A description of a blood glucose sensor circuit can be found in Steil et al., U.S. Pat. No. 6,558,351, filed Jun. 1, 2000.

Returning to FIG. 2, the action presented by the I/O module 210 may include prompting the user to begin a test or a series of tests in which blood glucose data is monitored and received into the device 200 via the I/O module 210. A test may be executed using an insulin pump. The rule module 215 applies the rule to at least one of the blood glucose data and the patient information to determine an insulin pump setting. In some examples, the rule module 215 generates an insulin pump setting that includes a target blood glucose level for the patient. The target blood glucose level may be a range of blood glucose levels.

Because a patient's basal insulin needs may change over time, such as with weight change or with a change in fitness level, basal rate testing may be performed periodically to ensure that an appropriate basal rate is being delivered by an insulin pump. Based on blood glucose data (e.g., the blood glucose level of the patient is not at the target blood glucose level), the rule module 215 may determine from the rule that a basal rate test should be run (by either the insulin pump included with the device 200 or a separate device). The I/O module 210 may present (such as by display) a suggestion to the user to execute a basal rate test. As a result of the basal rate test, the rule module 215 generates one or more basal rate patterns or profiles. The I/O module 210 may display a recommendation to change a programmable basal rate pattern of the insulin pump. Descriptions of devices and methods that perform a basal rate test are found in Blomquist et al., "Basal Rate Testing Using Frequent Blood Glucose Input," U.S. patent application Ser. No. 11/685,617, filed Mar. 13, 2007, which is incorporated herein by reference.

If a carbohydrate ratio is too small, the insulin pump may determine a carbohydrate bolus that is too large for the carbohydrates consumed. This may cause a low blood glucose level within a few hours of the carbohydrate bolus (e.g., the blood glucose level drops below 70 mg/dl). If a carbohydrate bolus is too large, the insulin pump may determine a carbohydrate bolus that is too small for the carbohydrates consumed. This may cause a high blood glucose level within a few hours of a carbohydrate bolus.

Based on the blood glucose data, the rule module 215 may determine that a recommendation to run a carbohydrate ratio test should be presented. As a result of the carbohydrate ratio test, the rule module 215 may generate a new carbohydrate ratio. The I/O module 210 may present a recommendation to change the carbohydrate ratio programmed in the insulin pump. In some examples, the rule module 215 may generate a carbohydrate insulin bolus pattern or profile to be delivered by the insulin pump. For example, the I/O module 210 may display a recommended carbohydrate bolus pattern that includes an extended carbohydrate bolus or a combination bolus. Descriptions of devices and methods that perform a carbohydrate ratio test are found in Blomquist, "Carbohydrate Ratio Testing Using Frequent Blood Glucose Input," U.S. patent application Ser. No. 11/679,712, filed Feb. 27, 2007, which is incorporated herein by reference.

It is important for an insulin pump to use an effective correction factor. If a correction factor for a pump is set too high, the blood glucose may not actually be dropping as much as estimated and could lead to high blood glucose levels. If the correction factor is set too low, a correction bolus may provide too much insulin and result in a low blood glucose level.

Based on the blood glucose data, the rule module 215 may apply the rule to the blood glucose data and present a recommendation that the user initiate a correction factor test. As a result of the correction factor test, the rule module 215 may generate a new a correction factor. The I/O module 210 may present a recommendation to change the correction factor programmed in the insulin pump. In some examples, the rule module 215 may generate an insulin correction bolus pattern or profile. For example, the I/O module 210 may display a recommended correction bolus such as a pattern including different correction factors for different times of the day for example. Descriptions of devices and methods that perform a carbohydrate ratio test are found in Blomquist et al., "Correction Factor Testing Using Frequent Blood Glucose Input," U.S. patent application Ser. No. 11/626,653, filed Jan. 24, 2007, which is incorporated herein by reference. If the device 200 includes an insulin pump, the controller 205 may executes one of the tests described.

The examples set forth above involved the device 200 recommending an action for the user to take based on the blood glucose data received into the device. In some examples, the rule module 215 may use the blood glucose data to first generate a question to be presented by the I/O module 210 before presenting an action. The rule module 215 generates the suggested insulin pump setting from application of the rule to the blood glucose data and patient information received in response to the question. For example, if the blood glucose data indicates blood glucose is low, the rule may include a look up table having a question as to whether the patient had a high activity level. If the device 200 receives a response through a user interface that the activity level was high, the look up table may include a recommended action corresponding to a table entry for low blood glucose and high activity. The table entry may include a recommended action that the patient eat before the activity or lower a programmable basal rate of insulin before, during, or after the activity.

In some examples, the controller 205 determines a rate of change of a blood glucose level of the patient from the blood glucose data. As an illustrative example, the controller 205 may determine that the blood glucose concentration level is increasing or decreasing at a rate of 2 to 4 mg/dl/min (milligrams per deciliter per minute). The rule module 215 may apply one or more rules to the rate of change of a blood glucose level to generate a suggested insulin pump setting. If the blood glucose level is high and increasing at a certain rate, the rule module 215 may apply the rule to generate an insulin correction bolus pattern.

The action presented by the I/O module 210 may be a test or tests that include a variety of steps. The tests may be included in the rule module 215 and are designed to obtain data or other information that is analyzed by the rule. The tests may occur over a series of days. For example, during the test the device 200 may instruct the insulin pump user to skip breakfast the first day, skip lunch the second day, and skip dinner the third day. The device 200 may display an action for the user that includes taking blood glucose measurements at specified times in the test, such as pre-meal, post-meal, and while fasting for example. The device 200 may ask the user to perform or not perform certain activities (e.g., exercise) during the testing. The device may present an action to the user to eat specific portions of food having specific nutritional content. As part of the test, the device 200 may ask the user to input patient information into the device 200 (e.g., through the user interface, or through a second separate device that communicates with the device 200 via a communication port). The patient information may include health information, stress level information, or other information pertinent to later test analysis.

After the testing, the device 200 presents one or more questions to the user. The questions and responses from the user are part of a post-test patient interview by the device 200. The information from the patient interview and the blood glucose data are then analyzed. The rule module 215 applies the rule to the responses during the interview, the blood glucose data obtained as part of the test, and any other test data. The rule module 215 generates changes to insulin therapy parameters. In some examples, the changes are presented to the user, and the user has the option of accepting the changes.

If the device 200 includes an insulin pump, the changes are adopted by the device 200. If the device is a computing device such as in FIG. 5, or a device that includes a GM that is separate from the insulin pump, the changes may be communicated to the insulin pump. According to some examples the functions can be accomplished using multiple devices. For example, a first device may guide the patient through the test or tests. This device may include an insulin pump such as the device 400 in FIG. 4. The patient interview and analysis may be done by a second device such as the device 500 in FIG. 5.

As set forth previously, a rule or set of rules may be customized, such as by a rule development module included in the controller 205 for example. In some examples, all or substantially all aspects of the rule are customizable, including the type of tests to run, the sequence of tests to run, the steps in the tests, and the criteria for making changes. An expert in the treatment of diabetes would customize the rules to suit their standard of practice.

According to some embodiments, the device 200 may present changes other than insulin pump therapy parameters. In some examples, the rule module 215 may generate a recommend change to a patient lifestyle, such as a recommendation to exercise more or to reduce smoking. The I/O module 210 presents the recommend changes to the lifestyle of the patient. In some examples, the rule module 215 may generate a recommend change to a patient diet, such as a recommendation to eat foods having a lower glycemic index or to consume less alcohol.

It is to be understood that the above description is intended to be illustrative, and not restrictive. For example, the above-described embodiments (and/or aspects thereof) may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own.

What is claimed is:

1. A device comprising:
   a controller including:
      an input/output (I/O) module configured to:
         present a question about patient information, including at least one of health information, lifestyle information, or demographic information, for a patient when communicatively coupled to a user interface; and
         receive patient information in response to the question via the user interface;
      a rule module configured to:
         apply a rule to the patient information, wherein the rule comprises a decision tree, look-up table or formula; and
         generate a device determined pump setting from application of the rule; and
      a rule editor that edits existing rules in addition to editing new rules and is configured to receive modifications to the rule via the I/O module; and
   a memory communicatively coupled to the controller for storing parameters associated with an initial pump setup.

2. The device of claim 1, including a communication port communicatively coupled to the controller, and wherein the I/O module is configured to:
   present the device determined pump setting using the device via the user interface;
   present a request for confirmation of the device determined pump setting; and
   receive a confirmation, and
   communicate the device determined pump setting via the communication port when a confirmation is received into the device.

3. The device of claim 1, wherein rule module is configured to generate at least one of a basal rate pattern, a correction factor, and a carbohydrate ratio.

4. The device of claim 1, wherein the patient information includes at least one of patient health information and patient lifestyle information.

5. The device of claim 1, wherein the rule development module is configured to:
   display a representation of the rule when the I/O module is communicatively coupled to a user interface that includes a display; and
   convert a manipulation of the representation via the user interface into the modifications to the rule.

6. The device of claim 1, wherein the I/O module is configured to present changes to a diet of the patient.

* * * * *